›

US009532980B2

(12) United States Patent
Flajolet et al.

(10) Patent No.: US 9,532,980 B2
(45) Date of Patent: Jan. 3, 2017

(54) METHODS FOR THE TREATMENT OF A-β RELATED DISORDERS AND COMPOSITIONS THEREFOR

(75) Inventors: Marc Flajolet, New York, NY (US); Paul Greengard, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 12/447,080

(22) PCT Filed: Oct. 24, 2007

(86) PCT No.: PCT/US2007/022519
§ 371 (c)(1),
(2), (4) Date: Jan. 29, 2010

(87) PCT Pub. No.: WO2008/066626
PCT Pub. Date: Jun. 5, 2008

(65) Prior Publication Data
US 2010/0143361 A1    Jun. 10, 2010

Related U.S. Application Data

(60) Provisional application No. 60/854,333, filed on Oct. 25, 2006.

(51) Int. Cl.
A61K 39/40       (2006.01)
A61K 39/42       (2006.01)
A61K 31/44       (2006.01)
A61K 31/40       (2006.01)
A61K 31/70       (2006.01)

(52) U.S. Cl.
CPC .............. *A61K 31/44* (2013.01); *A61K 31/40* (2013.01); *A61K 31/70* (2013.01)

(58) Field of Classification Search
None
See application file for complete search history.

(56) References Cited

U.S. PATENT DOCUMENTS

| 4,376,110 A | 3/1983 | David et al. |
| 4,946,778 A | 8/1990 | Ladner et al. |
| 5,530,101 A | 6/1996 | Queen et al. |
| 5,545,580 A | 8/1996 | Sheng et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,789,650 A | 8/1998 | Lonberg et al. |
| 5,880,141 A | 3/1999 | Tang et al. |
| 5,910,771 A | 6/1999 | Stumberg et al. |
| 5,932,448 A | 8/1999 | Tso et al. |
| 6,060,296 A | 5/2000 | Hoekstra et al. |
| 6,288,089 B1 | 9/2001 | Zawada et al. |
| 6,465,493 B1 | 10/2002 | Burgess et al. |
| 6,555,328 B1 | 4/2003 | Keesler et al. |
| 6,800,283 B2 | 10/2004 | Gong et al. |
| 7,129,073 B2 | 10/2006 | Liu et al. |
| 7,320,785 B2 | 1/2008 | Greengard et al. |
| 2003/0100514 A1 | 5/2003 | Ahotupa et al. |

FOREIGN PATENT DOCUMENTS

| WO | WO 99/32619 | 7/1999 |
| WO | WO 01/41768 | 6/2001 |
| WO | WO 2005/001114 | 1/2005 |
| WO | WO 2005/105987 | 11/2005 |

OTHER PUBLICATIONS

Agostinis, P. et al., *FEBS Lett.*, 1989, 259(1), pp. 75-78.
Amit, S. et al., *Genes Dev.*, 2002, 16, pp. 1066-1076.
Behrend et al., Oncogene 19, 2000, pp. 5303-5313.
Bird, *Science*, 1988, 242, pp. 423-426.
Chijiwa et al., *J. Biol. Chem*, 1989, 264, pp. 4924-4927.
Cote et al., *Proc. Natl. Acad Sci USA*, 1983, 80, pp. 2026-2030.
Cong, F. et al., *Mol Cell Biol.*, 2004, 24, 2000-2011.
Cotten et al., *Embo J.*, 1989, 8, pp. 861-3866.
Davidson, G. et al., *Nature*, 2005, 438, pp. 867-872.
Desdouits, F. et al., *Proc Natl Acad Sci USA*, 1995, 92, pp. 2682-2685.
Desjardins, PR et al., 1972, (12), pp. 1249-1259.
Fish et al., *J. Biol. Chem.* 1995, 270, pp. 14875-14883.
Ghoshal, N. et al., "A New Molecular Link between the Fibrillar and Granulovacuolar Lesions of Alzheimer's Disease", American Journal of Pathology, 1999, vol. 155, No. 4, pp. 1163-1172.
Gibson, *Cancer and Metastasis Reviews*, 1996, 15, pp. 287-299.
Godl, K. et al., *PNAS USA*, 2003, 100(26), pp. 15434-15439.
Gompel, M. et al., *Bioorg Med Chem Lett.*, 2004, 14(7), pp. 1703-1707.
Good et al., *Gene Therapy*, 1997, 4, pp. 45-54.
Grassi & Marini, *Annals of Medicine*, 1996, 28, pp. 499-510.
Gross, S.D. et al., *J. Cell Biol.*, 1995, 130, pp. 711-724.
Gross, S.D., et al., *Cell Signal*, 1998, pp. 699-711.
Huse et al., *Science*, 1989, 246, pp. 1275-1281.
Huston et al., *Proc. Natl. Acad. Sci. USA*, 1988, 85, pp. 5879-5883.
Inagaki, M., et al. *Mol. Pharmacol.*, 1986, 29, p. 577-581.
Inman et al., *Molecular Pharmacology*, 2002, 62, pp. 65-74.
Issinger, O.G., Pharmacol Ther., 1993, 59, pp. 1-30.
Joachim, C.L. et al., *Nature*, 1989, 341(6239), pp. 226-230.
Kloss, B. et al., *Neuron*, 2001, 30, pp. 699-706.
Kohler and Milstein, *Nature*, 1975, 256, pp. 495-497.
Kopan, R., et al., *Proc. Natl. Acad. Sci, U.S.A.*, 1996, 93, pp. 1683-1688.s.
Kozbor et al., *Immunology Today*, 1983, 4, p. 72.
Kusuda et al., *Genomics*, 1996, 32, pp. 140-143.
Liu, F. et al., *Proc Natl Acad Sci.*, 2001, 98, pp. 11062-11068.
Liu, S.J. et al., *J. Neurochem*, 2003, 87, pp. 1333-1344.
Lu et al., *Adv. Genet.*, 2005, 54, pp. 117-142.

(Continued)

*Primary Examiner* — Olga N Chernyshev

(57) ABSTRACT

The invention provides methods for treating Aβ peptide related disorders such as Alzheimer's disease comprising administering a therapeutically effective amount of a CK1 modulator to a patient in need thereof.

4 Claims, No Drawings

(56) References Cited

OTHER PUBLICATIONS

Mashhoon et al., "Crystal structure of a conformation-selective caseine kinase-1 inhibitor", *J. Biological Chemistry*, 2000, vol. 275, No. 26, pp. 20052-20060.
Massillon, D., *Biochem J.*, 1994, 299 (Pt 1), pp. 123-128.
Matsumura, S. and Takeda, M., *Biochim Biophys Acta.* 1972, 289(1), pp. 237-241.
Meggio, F. et al., *Eur J Biochem.*, 1990, 187(1), pp. 89-94.
Meijer, L. et al., *Chem Biol.*, 2000, (1), pp. 51-63.
Meijer, L. et al., *Trends Pharmacal Sci.*, 2004, 25, pp. 471-480.
Miller et al., *Cell Mol. Neurobiol.*, 2005, 25, pp. 1195-1207.
Morrison et al., *Proc. Natl. Acad. Sci.*, 1984, 81, pp. 6851-6855.
Netzer, W.J., et al., *Proc. Natl. Acad. Sci. U.S.A.*, 2003, 100(21), pp. 12444-12449.
Neuberger et al., *Nature*, 1984, 312, pp. 604-608.
Pastorino, L. et al., *Mo. Cell Neurosci.*, 2002, 19, pp. 175-185.
Reinhardt, J. et al., "Purification of CK1 by affinity chromatography on immobilized axin", *Protein Expression and Purcation*, 2007, vol. 54, pp. 101-109.
Rena et al., "D4476, a cell-permeant inhibitor of CK1, suppresses the site-specific phosphorylation and nuclear exclusion of FOXO1a", *EMBO Reports*, 2004, vol. 5, No. 1, pp. 60-65.
Schwab, C. et al., "Casein kinase 1 delta is associated with pathological accumulation of tau in several neurodegenerative diseases", *Neurobiology of Aging*, vol. 21, 2000, pp. 503-510.
Singh, T.J. et al., *FEBS Lett.*, 1995, 358, pp. 267-272.
Takeda et al., *Nature*, 1985, 314, pp. 452-454.
Turner, E.J.H. et al., *Br. J. Haematol*, 2003, 120, p. 894.
Vancura, A. et al., *J. Biol Chem.*, 1994, 269, pp. 19271-19278.
Ueno, T., et al., *Pathology International*, 2003, vol. 53, pp. 265-269.
Walter et al., "Phosphorylation regulation intracellular trafficking of beta-secretase", *J. Biological Chemistry*, 2001, vol. 276, No. 18, pp. 14634-14641.
Walter, J. et al., *Biochemistry*, 1998, 37, pp. 5961-5967.
Walter, J., et al., *J. Biol. Chem.*, 2000, vol. 275, No. 31, pp. 23523-23529.
Walter, J. et al., *J. Biol. Chem.*, 1996, 271, pp. 111-119.
Ward et al., *Nature*, 1989, 341, pp. 544-546.
Xu, H., et al., *Nat. Med.*, 1998, 4, pp. 447-451.d.
Yasojima et al., "Casein kinase 1 delta mRNA is upregulated in Alzheimer disease brain", *Brain Research*, 2000, vol. 865, pp. 116-120.
Yokoyama, T. et al., *Biol Pharm Bull.*, 2003, (3), pp. 371-374.
Zhai, L. et al., *J. Biol. Chem.*, 1995, vol. 270, pp. 12717-12724.
Ahmed, K., *Cell Mol Biol Res.*, 1994, 40, pp. 1-11.

METHODS FOR THE TREATMENT OF A-β RELATED DISORDERS AND COMPOSITIONS THEREFOR

CROSS REFERENCE TO RELATED APPLICATIONS

This application is a U.S. National Stage application under 35 U.S.C. 371 claiming benefit of PCT Application No. PCT/US2007/022519, filed on Oct. 24, 2007, which claims the benefit of U.S. Provisional Application No. 60/854,333, filed on Oct. 25, 2006, the contents of each of which are incorporated herein by reference.

STATEMENT REGARDING GOVENRNMENT FUNDING

This invention was made; with government support under Grant. No. DAMD17-02-1-0705 awarded by DOD/USAM-RAA. The government has certain rights in the invention.

TECHNICAL FIELD

The present invention relates to a new use of CK1 inhibitors in the treatment of diseases involving the over production of Amyloid-β (Abeta or Aβ) peptide, such as Alzheimer's disease (AD).

BACKGROUND OF THE INVENTION

It is widely accepted that Aβ peptide is a causative agent in the development of Alzheimer's disease. Aβ peptides are metabolites of Amyloid-β precursor protein (Alzheimer's disease-associated precursor protein or APP), and consist mainly of 40 to 42 amino acids, Aβ1-40 ("Aβ40") and Aβ1-42 ("Aβ42"), respectively. Aβ40 and Aβ42 are generated by two enzymatic cleavages occurring close to the C-terminus of APP. The enzymes responsible for the cleavage, the aspartyl protease beta-secretase ("BACE") and the presenilin-dependent protease γ-secretase ("γ-secretase"), generate the N- and C-termini of Aβ, respectively. The amino terminus of Aβ is formed by β-secretase cleavage between methionine residue 596 and aspartate residue 597 of APP (numbering based on APP 695 isoform). γ-secretase cleaves at varying positions (38-, 40- or 43-residues C-terminal of this β-secretase cleavage product) to release the Aβ peptides. A third enzyme, α-secretase, cleaves the precursor protein between the β- and γ-cleavage sites, thus precluding Aβ production and releasing an approximately 3 kDa peptide known as P3, which is non-pathological. Both β- and α-secretase cleavage also result in soluble, secreted-terminal fragments of APP, known as sAPPβ and sAPPα, respectively. The sAPPα fragment has been suggested to be neuroprotective. These secretases may also be involved in the processing of other important proteins. For example, γ-secretase also cleaves Notch-1 protein.

In normal individuals, the Aβ peptide is found in two predominant forms, the majority Aβ-40 (also known as Aβ1-40 form and the minority Aβ42 (also known as Aβ-42) form, each having a distinct COOH-terminus. The major histological lesions of AD are neuritic plaques and neurofibrillary tangles occurring in affected brain regions. Neuritic plaques consist of AP peptides, primarily Aβ40 and Aβ42. Although healthy neurons produce at least ten times more Aβ40 compared to Aβ42, plaques contain a larger proportion of the less soluble Aβ42. Patients with the most common form of familial Alzheimer's disease show an increase in the amount of the Aβ42 form. The Aβ40 form is not associated with early deposits of amyloid plaques. In contrast, the Aβ42 form accumulates early and predominantly in the parenchymal plaques and there is strong evidence that Aβ42 plays a major role in amyloid plaque deposits in familial Alzheimer's disease patients. Neurofibrillary tangles consist of aggregated tau protein and their role in AD pathology is less clear. AD symptoms are most closely correlated with total brain Aβ rather than plaques. About 10% of AD cases result from autosomal dominant inheritance of mutations in either the APP or the presenilin 1 and presenilin 2 genes. In both cases, increased production of total AP or Aβ42 versus Aβ40 results.

As discussed above, Alzheimer's disease is widely believed to be associated with accumulation of the neurotoxic peptide Aβ. While Aβ is produced by sequential cleavage of APP by BACE and γ-secretase, major efforts to develop selective inhibitors of these enzymes have met with only limited success. For example, most γ-secretase inhibitors suffer from the drawback that they inhibit the cleavage of Notch, a protein essential for normal development.

In addition to BACE and γ-secretase, Casein Kinase 1 ("CK1") has also been implicated in the production of Aβ-40 and Aβ-42 peptides. For example, CK1δ mRNA has been shown to be up-regulated in AD brain samples (Yasojima, K. et al. (2000) Brain Res 865, 116-20) and may be associated with a pathological association with tau (Schwab, C. et al., (2000) Neurobiol Aging 21, 503-10). Interestingly, Glycogen Synthase Kinase 3 (GSK-3), one of the most studied kinases in the Alzheimer field, can phosphorylate its substrates only if they are pre-phosphorylated by a priming kinase, and CK1 is one of the few GSK-3 priming kinases (PKA, CK1, CK2, Cdk5 and DYRK1A) (See e.g., Meijer, L. et al., (2004) Trends Pharmacol Sci 25, 471-80). It has also been shown that CK1 is an upstream regulator of Cdk5, another protein kinase implicated in AD (Liu, F. et al., (2001) Proc Natl Acad Sci USA 98, 11062-8). Moreover, CK1 phosphorylates BACE, and regulates its subcellular location (Pastorino, L., Ikin, A. F., Nairn, A. C., Pursnani, A. & Buxbaum, J. D. (2002) Mol Cell Neurosci 19, 175-85.). CK1 has also been shown to phosphorylate PS2 (Walter, J., Grunberg, J., Schindzielorz, A. & Haass, C. (1998) Biochemistry 37, 5961-7.

In mice, CK1 consists of a family of eight genes that appear to function as monomeric enzymes: α, γ1, γ2, γ3, δ, ε1, ε2 and ε3. Family members contain a highly conserved 290 residue N-terminal catalytic domain coupled to a variable C-terminal region that ranges in size from 40 to 180 amino acids. It is possible that the different isoforms are expressed in different neuronal populations and/or are targeted to different regions of the neuron, and thus may have access to different substrates. Little is known about the regulation of CK1. CK1 is basally active but certain isoforms (particularly CK1δ and ε) are regulated by inhibitory autophosphorylation at their C-terminal regions (Zhai, L. et al., (1995) J Biol Chem 270, 12717-24). Notably, it has been shown that the C-terminal region of CK1ε is phosphorylated at multiple sites and that enzyme activity can be increased following dephosphorylation by a signaling pathway involving activation of the serine/threonine phosphatase, calcineurin in response to stimulation of metabotropic glutamate receptors in neurons (Liu, F., et al., (2001) Proc Natl Acad Sci U S A 98, 11062-8; Liu, S. J. et al., (2003) J Neurochem 87, 1333-44).

CK1 is localized to both the cytosol and the nucleus; the C-terminal region of CK1 has been shown to promote differential subcellular localization of individual isoforms (e.g. nucleus versus cytoplasm). A number of proteins have been found to interact with CK1 isoforms in non-neuronal tissues resulting in its targeting to specific signaling pathways (Amit, S., et al. (2002) *Genes Dev* 16, 1066-76; Cong, F., et al., (2004) *Mol Cell Biol* 24, 2000-11; Davidson, G., et al., (2005) *Nature* 438, 867-72).

Association of CK1 with the plasma membrane and the cytoskeleton has also been reported. (Ahmed, K. (1994) *Cell Mol Biol Res* 40, 1-11; Vancura, A. et al., (1994) *J Biol Chem* 269, 19271-8; Walter, J., Schnolzer, M., Pyerin, W., Kinzel, V. & Kubler, D. (1996) *J Biol Chem* 271, 111-9). In neurons, CK1 phosphorylates a variety of proteins including transcriptional factors, as well as certain synaptic vesicle proteins (Issinger, 0. G. (1993) *Pharmacol Ther* 59, 1-30; Gross, S. D. et al. (1995) *J Cell Biol* 130, 711-24). CK1δ and CK1ε, being predominantly expressed in brain (Gross, S. D. & Anderson, R. A. (1998) *Cell Signal* 10, 699-711), have been implicated in several important brain processes, including but not limited to: dopamine signaling (DARPP-32 phosphorylation), circadian rhythm (mPer phosphorylation) and brain receptor signaling (Desdouits, F., et al., (1995) *Proc Natl Acad Sci USA* 92, 2682-5; Kloss, B., et al. (2001) *Neuron* 30, 699-706; Singh, T. J. et al. (1995) *FEBS Lett* 358, 267-72.

SUMMARY OF THE INVENTION

We have now surprisingly discovered that constitutively active CK1ε increases the formation of (β-amyloid and that CK1 inhibitors can reduce the formation of β-amyloid peptide produced in cells expressing endogenous levels of CK1 as well as over-expressing constitutively active CK1ε. Significantly, under conditions in which inhibition of CK1 activity reduces β-amyloid formation, no inhibition of Notch cleavage is observed. Experiments demonstrate that the effects of CK1 is expressed at the level of the γ-secretase cleavage site. Thus, CK1 provides a novel drug target for Aβ related disorders, including AD. The instant invention also provides a method for identifying modulators of CK1 activity, and/or CK1 gene expression and for using such modulators for the treatment of Aβ related disorders in human and veterinary patients. The invention also provides pharmaceutical compositions comprising said modulators.

The instant application relates to the discovery that CK1 is a suitable target for the development of new therapeutics to treat conditions characterized by overproduction of Aβ peptide, referred to collectively herein as "Aβ related disorders" and which includes, but is not limited to, AD. Thus, in one aspect the invention relates to a method to identify modulators useful to treat Aβ related disorders, including Alzheimer's disease, comprising: a) assaying for the ability of a candidate modulator to inhibit the activity of CK1 and/or inhibit CK1 gene expression in vitro or in vivo and which can further include b) assaying for the ability of an identified inhibitory modulator to reverse the pathological effects observed in animal models of Alzheimer's disease and/or in clinical studies with subjects with Alzheimer's disease.

For example, the invention relates to a method (Method 1) to treat, control or manage Aβ related disorders, including Alzheimer's disease, comprising administering to a subject in need thereof a CK1 modulator in an amount effective to inhibit or reduce accumulation of Aβ peptide, preferably a CK1ε modulator, wherein said modulator, e.g., inhibits the enzyme activity of CK1 and/or inhibits CK1 gene expression in said subject, or modifies CK1 subcellular localization or modulates CK1 protein stability, e.g., in accordance with any of the following methods:

1.1 Method 1 wherein the Aβ related disorder is any disease characterized by accumulation of abnormal protein aggregates, especially in the brain, e.g., amyloid plaques and neurofibrillary tangles, for example precipitates of tau or amyloid proteins, e.g., Aβ;

1.2 Method 1 or 1.1 wherein the disease is selected from Alzheimer's disease, progressive supranuclear palsy, Down's Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins, e.g., Aβ;

1.3 Any of the preceding methods wherein the disease is Alzheimer's Disease;

1.4 Any of the preceding methods wherein the modulator is a CK1 inhibitor;

1.5 Any of the preceding methods wherein the modulator is an indolin-2-one derivative, e.g., IC261, in free or pharmaceutically acceptable salt form;

1.6 Any of the preceding methods 1-1.4 wherein the modulator is a triarylimidazole, e.g., D4476 or SB-431542 or SB-203580, in free or pharmaceutically acceptable salt form;

1.7 Any of the preceding methods 1-1.4 wherein the modulator is an isoquinoline sulfonamide e.g. CK1-7 in free or pharmaceutically acceptable salt form;

1.8 Any of the preceding methods 1-1.4 wherein the modulator is 5,6-dichloro-1-beta-D-ribofuranosyl-benzimidazole (DRB) in free or pharmaceutically acceptable salt form;

1.9 Any of the preceding methods 1-1.4 wherein the modulator is a pyrroloazepine derivative, e.g., hymenialdisine, in free or pharmaceutically acceptable salt form;

1.10 Any of the preceding methods 1-1.4 wherein the modulator is an amino pyrimidine-indole, e.g. matairesinol, in free or pharmaceutically acceptable salt form;

1.11 Any of the preceding methods 1-1.4 wherein the modulator is 5-iodotubercidin in free or pharmaceutically acceptable salt form;

1.12 Any of the preceding methods 1-1.4 wherein the modulator is meridianin E in free or pharmaceutically acceptable salt form;

1.13 Any of the preceding methods 1-1.4 wherein the modulator comprises any one or more substances selected from the group consisting of antisense oligonucleotides, triple helix DNA, ribozymes, RNA aptamers and double stranded RNA wherein said substances are designed to inhibit CK1 gene expression;

1.14 Any of the preceding methods 1-1.4 wherein the modulator comprises antibodies to CK1 or fragments thereof;

1.15 Method 1.14 wherein said antibodies can e.g., inhibit CK1 kinase activity, modify CK1 sub-cellular localization or modulate CK1 protein stability;

1.16 Any of the foregoing methods additionally comprising administering an effective amount of an acetylcholinesterase inhibitor;

1.17 Method 1.16 wherein the acetylcholinesterase inhibitor is selected from donepezil (Aricept), rivastigmine (Exelon), and galantamine (Reminyl) in free or pharmaceutically acceptable salt form;

1.18 Any of the foregoing methods 1-1.4, 1.16 or 1.17 comprising administering a composition in accordance with any of Compositions 1-1.17 below.

1.19 Any of the foregoing methods wherein the CK1 modulator specifically modulates CK1ε.

1.20 Any of the foregoing methods wherein the CK1 modulator is a compound capable of inhibiting CK1 activity with an $IC_{50}$ of less than 100 µM, e.g., wherein the CK1 activity is defined as the activity of CK1 enzyme to phosphorylate a peptide based on the CK1 phosphorylation site at the Ser-22 residue of µ-casein A2 protein (e.g., Asp-Asp-Asp-Glu-Glu-Ser-Ile-Thr-Arg-Arg, Seq. Id No. 1), e.g. as described in Agostinis P, et al. FEBS Lett. 1989 Dec 18;259(1):75-8.

In another aspect, the invention relates to a method to treat Aβ related disorders, including Alzheimer's disease, comprising administering to a subject in need thereof a pharmaceutical composition comprising an effective amount of a CK1 modulator, e.g., a modulator as described in any of methods 1-1.15 above. In various embodiments, said pharmaceutical composition comprises any of the CK1 modulators discussed above.

In another aspect, the invention relates to a pharmaceutical composition (Composition 1) comprising a CK1 modulator, e.g., in an amount effective to treat Aβ related disorders, including Alzheimer's disease, by inhibiting or reducing the accumulation of Aβ peptide in a subject in need thereof, wherein said modulator, e.g., can inhibit the enzymatic activity of CK1 or modify CK1 protein stability or sub-cellular localization and/or inhibit CK1 gene expression, in combination or association with a pharmaceutically acceptable diluent or carrier; e.g., in accordance with any of the following compositions:

1.1 Composition 1 wherein the Aβ related disorder is any disease characterized by accumulation of abnormal protein aggregates, especially in the brain, e.g., amyloid plaques and neurofibrillary tangles, for example precipitates of tau or amyloid proteins, e.g., Aβ;

1.2 Composition 1 or 1.1 wherein the disease is selected from Alzheimer's disease, progressive supranuclear palsy, Down's Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins, e.g., Aβ;

1.3 Any of the preceding compositions wherein the disease is Alzheimer's Disease;

1.4 Any of the preceding compositions wherein the modulator is a CK1 inhibitor;

1.5 Any of the preceding compositions wherein the modulator is an indolin-2-one derivative, e.g., IC261, in free or pharmaceutically acceptable salt form;

1.6 Any of the preceding compositions 1-1.4 wherein the modulator is a triarylimidazole, e.g., D4476 or SB-431542 or SB-203580, in free or pharmaceutically acceptable salt form;

1.7 Any of the preceding compositions 1-1.4 wherein the modulator is an isoquinoline sulfonamide e.g. CK1-7 in free or pharmaceutically acceptable salt form;

1.8 Any of the preceding compositions 1-1.4 wherein the modulator is 5,6-dichloro-1-beta-D-ribofuranosyl-benzimidazole (DRB) in free or pharmaceutically acceptable salt form;

1.9 Any of the preceding compositions 1-1.4 wherein the modulator is a pyrroloazepine derivative, e.g., hymenialdisine, in free or pharmaceutically acceptable salt form;

1.10 Any of the preceding compositions 1-1.4 wherein the modulator is an amino pyrimidine-indole, e.g. matairesinol, in free or pharmaceutically acceptable salt form;

1.11 Any of the preceding compositions 1-1.4 wherein the modulator is 5-iodotubercidin in free or pharmaceutically acceptable salt form;

1.12 Any of the preceding compositions 1-1.4 wherein the modulator is meridianin E in free or pharmaceutically acceptable salt form;

1.13 Any of the preceding compositions 1-1.4 wherein the modulator comprises any one or more substances selected from the group consisting of antisense oligonucleotides, triple helix DNA, ribozymes, RNA aptamers and double stranded RNA wherein said substances are designed to inhibit CK1 gene expression;

1.14 Any of the preceding compositions 1-1.4 wherein the modulator comprises antibodies to CK1 or fragments thereof;

1.15 Composition 1.14 wherein said antibodies can e.g., inhibit CK1 kinase activity, modify CK1 sub-cellular localization or modulate CK1 protein stability;

1.16 Any of the foregoing compositions further comprising an effective amount of an acetylcholinesterase inhibitor;

1.17 Composition 1.16 wherein the acetylcholinesterase inhibitor is selected from donepezil, rivastigmine, and galantamine, in free or pharmaceutically acceptable salt form.

1.18 Any of the foregoing compositions wherein the CK1 modulator is a compound capable of inhibiting CK1 activity with an $IC_{50}$ of less than 100 µM, e.g., wherein the CK1 activity is defined as the activity of CK1 enzyme to phosphorylate a peptide based on the CK1 phosphorylation site at the Ser-22 residue of β-casein A2 protein (e.g., Asp-Asp-Asp-Glu-Glu-Ser-Ile-Thr-Arg-Arg, Seq. Id No. 1), e.g. as described in Agostinis P, et al. FEBS Lett. 1989 December 18;259(1):75-8.

In another aspect, the invention relates to a method to diagnose subjects suffering from an Aβ related disorder, including Alzheimer's disease, who may be suitable candidates for treatment with CK1 modulators comprising detecting levels of this protein in a biological sample from said subject wherein subjects with increased levels compared to normal controls would be suitable candidates for CK1 modulator treatment.

In yet another aspect, the invention relates to a method to diagnose a subject suffering from an Aβ related disorder, including Alzheimer's disease, who may be a suitable candidate for treatment with CK1 modulators comprising assaying mRNA levels of this protein in a biological sample from said subject wherein a subject with increased levels compared to normal controls would be suitable candidates for CK1 modulator treatment.

In yet another aspect, there is provided a method to treat Aβ related disorders, including Alzheimer's disease, comprising: (a) assaying for CK1 mRNA and/or protein levels in a subject; and (b) administering to a subject with increased levels of CK1 mRNA and/or protein levels compared to controls a CK1 modulator in an amount sufficient to treat the pathological effects of the Aβ related disorder, e.g., in an amount sufficient to reduce formation of Aβ plaques, e.g., in accordance with any of Methods 1-1.20 supra.

In yet another aspect of the present invention there are provided assay methods and kits comprising the components necessary to detect expression of polynucleotides encoding CK1 or related regulatory polypeptides, or CK1 substrates, or levels of CK1 or related regulatory polypeptides, or CK1 substrates or fragments thereof, in body tissue samples derived from a patient, such kits comprising, e.g., antibodies that bind to said polypeptides or substrates, or to fragments thereof, or oligonucleotide probes that hybridize with said polynucleotides. In a preferred embodiment, such kits also comprise instructions detailing the procedures by which the kit components are to be used.

The present invention also pertains to the use of a CK1 modulator in the manufacture of a medicament for the treatment or amelioration of an Aβ related disorder, including Alzheimer's disease, e.g., wherein the modulator is as set forth in any of Methods 1-1.20 or wherein the medicament is a composition in accordance with any of Compositions 1-1.18.

DETAILED DESCRIPTION OF THE INVENTION

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication which might be used in connection with the invention.

In practicing the present invention, many conventional techniques in molecular biology may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: . A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively.

As used herein and in the appended claims, the singular forms "a", "an", and "the" include plural reference unless the context clearly dictates otherwise. Thus, for example, reference to the "antibody" is a reference to one or more antibodies and equivalents thereof known to those skilled in the art, and so forth.

The term "Aβ", "Aβ peptide", "amyloid β" and the like are synonymous, and refer to one or more peptide components of about 38-43 amino acids derived from beta amyloid precursor protein (β-APP), as described hereinabove.

The term "CK1" refers to the polypeptide Casein Kinase 1 Desjardins PR et al, 1972 December 50(12):1249-59; Matsumura S. and Takeda M. Biochim Biophys Acta. 1972 November 10;289(1):237-41; Gross S D and Anderson R A. Cell Signal. 1998 November;10(10):699-711). The term refers to any and all forms of this polypeptide including, but not limited to, homologs, partial forms, isoforms, precursor forms, the full length polypeptide, fusion proteins containing the CK1 sequence or fragments of any of the above, from human or any other species. Indeed, numerous isoforms of CK1 have been identified and include, but are not limited to α, γ1, γ2, γ3, δ, ε1, ε2, ε3 isoforms. CK1 and its various isoforms are familiar to one of skill in the art and have been disclosed; see, e.g.,: GenBank Accession Numbers P48729, P48730, BC006490, P49674, Q9Y6M4, P78368, Q9HCP0 (as of Oct. 16, 2006), U.S. Pat. Nos. 6,555,328; 6,800,283; 6,060,296; Fish et al. J. Biol. Chem. 270:14875-14883, 1995; Guo et al. Int. J. Mol. Med. 10:227-230, 2002; Kusuda et al. Genomics 32:140-143, 1996 which are all incorporated by reference herein in their entireties. It is also contemplated that the term refers to CK1 isolated from naturally occurring sources of any species such as genomic DNA libraries as well as genetically engineered host cells comprising expression systems, or produced by chemical synthesis using, for instance, automated peptide synthesizers or a combination of such methods. Means for isolating and preparing such polypeptides are well understood in the art.

The words "treatment" and "treating" are to be understood accordingly as embracing prophylaxis and treatment or amelioration of symptoms of disease as well as treatment of the cause of the disease.

"Pathological effects of Aβ related disorders", "symptoms of Aβ related disorders" and like terms refer to, but are not limited to, memory dysfunction (which can range from mild forgetfulness to severe and debilitating memory loss), neurodegeneration, the formation and/or presence of senile plaques and/or neurofibrillary tangles and neuronal cell loss.

The ability of a substance to "modulate" CK1 (e.g., a CK1 modulator) refers to, but is not limited to, the ability of a substance to inhibit the enzymatic activity of CK1, or modulate the subcellular localization of the protein, or alter the stability of the protein (e.g., by post-translational modification such as phosphorylation, glycosylation, etc.) and/or inhibit CK1 gene expression. Such modulation could also involve effecting the ability of other proteins to interact with CK1, for example related regulatory proteins or proteins that are modified by CK1 and/or CK1 substrates.

"Nucleic acid sequence", as used herein, refers to an oligonucleotide, nucleotide or polynucleotide, and fragments or portions thereof, and to DNA or RNA of genomic or synthetic origin that may be single or double stranded, and represent the sense or antisense strand. "Polynucleotide" as used herein refers to DNA or RNA.

The term "double stranded RNA" as used herein is meant to encompass any and all conventional techniques for RNAi-mediated gene silencing. Such techniques are familiar to one of skill in the art and may include, but are not limited to, use of dsRNA, siRNA and shRNA to knockdown gene expression.

The term "antisense" as used herein, refers to nucleotide sequences that are complementary to a specific DNA or RNA sequence. The term "antisense strand" is used in reference to a nucleic acid strand that is complementary to the "sense' strand. Antisense molecules may be produced by any method, including synthesis by ligating the gene(s) of interest in a reverse orientation to a viral promoter that permits the synthesis of a complementary strand. Once introduced into a cell, this transcribed strand combines natural sequences produced by the cell to form duplexes. These duplexes then block either the further transcription or translation. The designation "negative" is sometimes used in reference to the antisense strand, and "positive" is sometimes used in reference to the sense strand.

As contemplated herein, antisense oligonucleotides, triple helix DNA, RNA aptamers, ribozymes and double stranded RNA are "directed to a nucleic acid sequence of CK1" such that the nucleotide sequence of CK1 chosen will produce gene-specific inhibition of CK1 gene expression. For example, knowledge of the CK1 nucleotide sequence may be used to design an antisense molecule which gives strongest hybridization to the mRNA. Similarly, ribozymes can be synthesized to recognize specific nucleotide sequences of CK1 and cleave it (Cech. J. Amer. Med Assn. 260:3030 (1988). Techniques for the design of such molecules for use in targeted inhibition of gene expression are well known to one of skill in the art.

The term "sample" as used herein, is used in its broadest sense. A biological sample from a subject may comprise blood, urine or other biological material with which CK1 protein levels, activity or gene expression may be assayed. A biological sample may include neuronal material such as brain biopsies and especially cortical or neocortical biopsies (e.g. middle frontal gyrus (Brodmann area 8); inferior frontal gyrus (Brodmann area 44); anterior cingulate gyrus (Brodmann area 32); superior, middle, and inferior temporal gyri (Brodmann areas 22, 21, and 20, respectively); the entorhinal cortex (Brodmann area 36/28); the inferior parietal lobule (Brodmann area 7); and the primary visual cortex (Brodmann area 17)) or non-neuronal sample such as blood cells, cerebrospinal fluid, or skin biopsies (as described, for example, for Aβ peptide in Joachim C L et al., Nature, 1989 Sep. 21;341(6239):226-30) from which total RNA may be purified for gene expression profiling using conventional glass chip microarray technologies such as Affymetrix chips, RT-PCR or other conventional methods.

As used herein, the term "antibody" refers to intact molecules as well as fragments thereof, such as Fa, F(ab')$_2$, and Fv, which are capable of binding the epitopic determinant. Antibodies that bind CK1 polypeptides can be prepared using intact polypeptides or fragments containing small peptides of interest as the immunizing antigen. The polypeptides or peptides used to immunize an animal can be derived from the translation of RNA or synthesized chemically, and can be conjugated to a carrier protein, if desired. Commonly used carriers that are chemically coupled to peptides include bovine serum albumin and thyroglobulin. The coupled peptide is then used to immunize an animal (e.g., a mouse, a rat or a rabbit).

The term "humanized antibody" as used herein, refers to antibody molecules in which amino acids have been replaced in the non-antigen binding regions in order to more closely resemble a human antibody, while still retaining the original binding ability.

A "therapeutically effective amount" is the amount of drug (e.g., CK1 modulator) sufficient to treat an Aβ related disorder. For example, a therapeutically effective amount of a CK1 modulator may be an amount to prevent the pathological accumulation of Aβ peptide that is seen in Alzheimer's disease.

"Molecular regulators of CK1 activity", "related regulatory proteins", "related regulatory polypeptides" and like terms, as used herein, refer to polypeptides involved in the regulation of CK1 which may be identified by one of skill in the art using conventional methods such as described herein.

An "Aβ related disorder" as defined herein includes, but is not limited to, any physical or mental disorder characterized by an abnormal level of Aβ peptides (of any size) compared to levels in healthy controls. Such disorders include but are not limited to, any and all forms of Alzheimer's disease, including Early-onset Alzheimer's, Late-onset dementia, and Familial Alzheimer's disease (FAD), mild cognitive impairment as well as any other condition mediated or affected by abnormal production of Aβ such as hereditary cerebral hemorrhage (cerebral amyloid angiopathy), Down's Syndrome, or Parkinson's disease.

"Subject" refers to any human or nonhuman organism.

The invention is based on the surprising discovery that over expression of constitutively active CK1ε leads to an increase in Aβ peptide production. This observation has led to the additional discovery that several structurally dissimilar CK1 inhibitors significantly reduce endogenous Aβ peptide production. Thus, CK1 is a useful drug target for the development of therapeutics for the treatment of Alzheimer's disease, a disease state not previously known to involve CK1 proteins.

Thus, in one aspect the invention relates to a method to identify modulators useful to treat Aβ related disorders, including but not limited to, Alzheimer's disease comprising: a) assaying for the ability of a candidate modulator to modulate the activity of CK1 and/or modulate CK1 gene expression in vitro or in vivo and which can further include b) assaying for the ability of an identified modulator to reverse the pathological effects observed in animal models of Alzheimer's disease and/ or in clinical studies with subjects with Alzheimer's disease. In a particular aspect, said modulator can inhibit the activity of CK1 and/or inhibit CK1 gene expression.

Conventional screening assays (both in vitro and in vivo) may be used to identify modulators (e.g., inhibitors) of CK1 kinase activity and/or CK1 gene expression. CK1 activity levels can be assayed in a subject using a biological sample from the subject using conventional enzyme activity assay methods. For example, CK1 activity may be assayed using a purified recombinant CK1 enzyme (e.g., produced using conventional baculovirus technology) and a synthetic peptide (Asp-Asp-Asp-Glu-Glu-Ser-Ile-Thr-Arg-Arg) (Seq. Id No. 1) which is based on the CK1 phosphorylation site at the Ser-22 residue of β-casein A2 protein as substrate, e.g. as described in Agostinis P, et al. FEBS Lett. 1989 Dec. 18;259(1):75-8. This peptide is useful to identify specific CK1 activity as it is known to be phosphorylated by CK1 but not by other typical Ser-Thr kinases such as casein kinase-2 (CK-2), PKA and PKC. Phosphorylation by CK1 occurs at Ser-6 of this peptide (corresponding to Ser-22 of the β-casein A2protein), the Thr-8 being unaffected. The $K_m$ for the peptide is higher (1 mM) than for β-casein A2 protein (40 μM), while the $V_{max}$ is quite comparable (Agostinis P, et al. FEBS Lett. 1989 Dec. 18;259(1):75-8). The enzymatic activity of CK1 may be measured after 30 minutes of incubation at 37° C. with both the recombinant enzyme (CK1) and the peptidic substrate in the presence of radiolabeled ATP. This activity may then be reevaluated in the presence of increasing concentrations of compounds to be tested, optionally using a known CK1 inhibitor as a positive control. $IC_{50}$ values of these compounds may be estimated from dose-response curves; compounds giving a micromolar range (less than 100 μM) inhibition would be of particular interest for further assay, bearing in mind that the $K_m$ for the peptide is higher than for the native protein.

CK1 gene expression (e.g. mRNA levels) may also be determined using methods familiar to one of skill in the art, including, for example, conventional Northern analysis, real time PCR or commercially available microarrays. Additionally, modulation by a test compound (e.g., inhibition) of CK1 and/or related regulatory protein levels and/or CK1 substrates can be detected with an ELISA antibody-based assay or fluorescent labeling reaction assay. These techniques are readily available for high throughput screening and are familiar to one skilled in the art. Data gathered from these studies may be used to identify those modulators with therapeutic usefulness for the treatment of an Aβ related disorder. For example, possible useful modulators to treat Alzheimer's disease could then be further assayed in conventional live animal models of Alzheimer's disease and/or in clinical trials with humans with Alzheimer's disease according to conventional methods to assess the ability of said modulator to prevent or ameliorate the pathological effects of Alzheimer's disease in vivo.

Candidate modulators for analysis according to the methods disclosed herein include chemical compounds known to inhibit CK1 as well as compounds whose effects on this protein at any level have yet to be characterized. Compounds known to possess modulatory activity could be directly assayed in animal models familiar to one of skill in the art or in clinical trials.

It is contemplated herein that any compound with CK1 inhibitory activity, and not necessarily only those compounds that specifically inhibit only CK1, may prove to be useful therapeutics. For example, mixed CK1 inhibitors (e.g., compounds that can inhibit some isoforms of CK1 but not others) may be useful in the instant invention.

CK1 inhibitors include, but are not limited to, compounds often having at least one imidazole ring (i.e. a heterocyclic compound that contains two nitrogen atoms in a five-membered ring) or one pyrroline ring (i.e., a heterocyclic compound that contains one nitrogen atoms in a five-membered ring) . In some cases, the five-membered ring containing one or two nitrogen atoms is fused or substituted with at least one six-membered ring lacking nitrogen atoms (benzene), or containing one nitrogen atom (pyridine) or containing two nitrogen atoms (pyrimidine).

Known CK1 inhibitors, including CK1 specific inhibitors, useful in the instant invention include, but are not limited to
  a. IC261: (3E)-3-[(2,4,6-trimethoxyphenyl)methylidene]-1 H-indol-2-one in free or pharmaceutically acceptable salt form; disclosed in Behrend et al., Oncogene 19: 5303-5313 (2000), Mashhoon et al., J Biol Chem 275: 20052-20060 (2000) and available from Calbiochem;
  b. Triarylimidazoles, e.g., as disclosed in U.S. Pat. No. 6,465,593 (incorporated herein by reference); e.g., D4476: 4-(4-(2,3-dihydrobenzo[1,4]dioxin-6-yl)-5-pyridin-2-yl-1H-imidazol-2-yl)benzamide in free or pharmaceutically acceptable salt form, e.g., as disclosed in Rena et al. EMBO Reports 5:60-65 (2004) and available from Calbiochem; and/or SB-431542: 4-(4-(benzo[1,3]dioxol-5-yl)-5-pyridin-2-yl-1H-imidazol-2-yl)benzamide, in free or pharmaceutically acceptable salt form, e.g., as disclosed in Inman et al., Molecular Pharmacology 62:65-74 (2002) and available from Sigma-Aldrich Chemical Co. ; or SB-203580: 4-(4-Fluorophenyl)-2-(4-methylsulfinylphenyl)-5-(4-pyridyl) 1 H-imidazole in free or pharmaceutically acceptable salt forms, e.g. as disclosed in Godl, K. et al PNAS USA 2003 Dec. 23;100(26): 15434-9 and available from BioSource International;
  c. CK1-7: disclosed in Chijiwa et al., J Biol Chem 264: 4924-4927 (1989);
  d. A3: N-(2-aminoethyl)-5-chloronaphthalene-1-sulfonamide, in free or pharmaceutically acceptable salt form, e.g., HCl salt; disclosed in Inagaki, M., et al. 1986. *Mol. Pharmacol.* 29: 577. Turner, E. J. H., et al. 2003. *Br. J. Haematol.* 120: 894, and available from Calbiochem;
  e. 5,6-dichloro-1-beta-D-ribofuranosyl-benzimidazole (DRB) in free or pharmaceutically acceptable salt forms, e.g. as disclosed in Meggio F. et al. *Eur J Biochem.* 1990 Jan. 12; 187(1):89-94, and available from Calbiochem;
  f. Pyrroloazepine derivatives, e.g., hymenialdisine, in free or pharmaceutically acceptable salt forms, e.g., as disclosed in Meijer L, et al. Chem Biol. 2000 January; 7(1):51-63 and available from BIOMOL International;
  g. Amino pyrimidine-indoles, e.g. matairesinol, in free or pharmaceutically acceptable salt forms, e.g. as disclosed in Yokoyama, T et al. Biol Pharm Bull. 2003 March; 26(3):371-4 and available from Cayman Chemical;
  h. 5-iodotubercidin in free or pharmaceutically acceptable salt forms, e.g., as disclosed in Massillon, D., Biochem J. 1994 Apr. 1;299 (Pt 1):123-8 and available from BIOMOL International; and
  i. Brominated 3-(2-aminopyrimidines)-indoles, e.g, meridianins, e.g., Meridianin E, in free or pharmaceutically acceptable salt forms, e.g., as disclosed in Gompel, M. et al. Bioorg Med Chem Lett. 2004 Apr. 5;14(7):1703-7.

It is contemplated herein that possible CK1 modulators may be a metabolite of a compound disclosed herein. It is further contemplated that a CK1 modulator may be chemically substituted to optimize the activity of the modulator, e.g., to improve solubility, to improve delivery across the blood brain barrier, to improve lipophylicity, and/or to reduce cell toxicity. Chemical modifications of this sort may be achieved according to conventional methods familiar to one of skill in the art.

In another aspect, the invention relates to a method to treat an Aβ related disorder including Alzheimer's disease comprising administering to a subject in need thereof a pharmaceutical composition comprising an amount of a CK1 modulator effective to inhibit accumulation of Aβ. Such modulators include antibodies directed to the CK1 polypeptide or fragments thereof. In certain embodiments, the pharmaceutical composition comprises antibodies that are highly selective for human CK1 polypeptides or portions of human CK1 polypeptides. Antibodies to CK1 may cause the aggregation of the protein in a subject and thus inhibit or reduce the activity of the kinase. Such antibodies may also inhibit or decrease CK1 activity, for example, by interacting directly with active sites or by blocking access of substrates to active sites. CK1 antibodies may also be used to inhibit CK1 activity by preventing protein-protein interactions that may be involved in the regulation of CK1 and necessary for kinase activity. CK1 antibodies could also affect CK1 subcellular localization by affecting, e.g., cellular diffusion or access to specific cellular compartments. Antibodies with inhibitory activity such as described herein can be produced and identified according to standard assays familiar to one of skill in the art.

CK1 antibodies may also be used diagnostically in conjunction with the methods of treatment described herein. For example, one could use these antibodies according to conventional methods to quantitate levels of CK1 in a subject; increased levels could indicate an Aβ related disorder or disposition thereto, so that the patient could then be treated with a CK1 inhibitor, e.g., in accordance with any of methods 1-1.20 above. In addition, for example, different CK1 levels could be indicative of various clinical forms or severity of Alzheimer's disease. Such information might also be useful to identify subsets of patients that may or may not respond to treatment with conventional therapies and for whom a particular therapy may be contraindicated and/or therapy with a CK1 modulator is preferred. Thus, it is contemplated herein that quantitating the message level of CK1 in a subject would be useful for diagnosis and determining appropriate therapy; subjects with increased mRNA levels of this protein compared to appropriate control individuals would be considered suitable candidates for treatment with CK1 inhibitors.

In another aspect, the present invention relates to a diagnostic kit which comprises:

(a) a polynucleotide of CK1 or a fragment thereof;
(b) a nucleotide sequence complementary to that of (a);
(c) a CK1 polypeptide, or a fragment thereof; or
(d) an antibody to a CK1 polypeptide.

It will be appreciated that in any such kit, (a), (b), (c) or (d) may comprise a substantial component. It is also contemplated that said kit could comprise components (a)-(d) designed to detect levels of CK1 related regulatory proteins or proteins modified by CK1 and/or CK1 substrates as discussed herein.

Similarly, it is contemplated herein that monitoring CK1 protein levels or kinase activity and/or detecting CK1 gene expression (mRNA levels) may be used as part of a clinical testing procedure, for example, to determine the efficacy of a given treatment regimen, e.g., in accordance with any of methods 1-1.20 above. For example, Alzheimer's patients undergoing conventional therapy may be evaluated and patients in whom CK1 levels, activity and/or gene expression levels are higher than desired (i.e. levels greater than levels in control patients) may be identified. Based on these data, the patient's dosage regimen may be adjusted and/or type of drug administered may be modified. It is contemplated herein that monitoring patient levels of CK1 as described above may provide a quantitative assessment of a patient's physical and/or mental state.

Factors for consideration for optimizing a therapy for a patient include the particular condition being treated, the particular mammal being treated, the clinical condition of the individual patient, the site of delivery of the active compound, the particular type of the active compound, the method of administration, the scheduling of administration, and other factors known to medical practitioners. The therapeutically effective amount of an active compound to be administered will be governed by such considerations, and is the minimum amount necessary for the treatment of an Aβ related disorder, preferably Alzheimer's disease.

Suitable antibodies to CK1 or related regulatory proteins or substrates may be obtained from a commercial source or produced according to conventional methods. For example, described herein are methods for the production of antibodies capable of specifically recognizing one or more differentially expressed gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

For the production of antibodies to the CK1 polypeptides discussed herein, for example, various host animals may be immunized by injection with the polypeptides, or a portion thereof. Such host animals may include, but are not limited to, rabbits, mice, and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with the polypeptides, or a portion thereof, supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:544-546) can be adapted to produce differentially expressed gene-single chain antibodies. Single chain antibodies are formed by linking the heavy and light chain fragments of the Fv region via an amino acid bridge, resulting in a single chain polypeptide.

Most preferably, techniques useful for the production of "humanized antibodies" can be adapted to produce antibodies to the polypeptides, fragments, derivatives, and functional equivalents disclosed herein. Such techniques are disclosed in U.S. Pat. Nos. 5,932,448; 5,693,762; 5,693,761; 5,585,089; 5,530,101; 5,910,771; 5,569,825; 5,625,126; 5,633,425; 5,789,650; 5,545,580; 5,661,016; and 5,770,429, the disclosures of all of which are incorporated by reference herein in their entirety.

Antibody fragments that recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275-1281) to allow rapid and easy identification of monoclonal Fab fragments with the desired specificity.

Detection of the antibodies described herein may be achieved using standard ELISA, FACS analysis, and standard imaging techniques used in vitro or in vivo. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$ $^{35}S$ or $^3H$.

Particularly preferred, for ease of detection, is the sandwich assay, of which a number of variations exist, all of which are intended to be encompassed by the present invention. For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex, a second antibody, labeled with a reporter molecule capable of inducing a detectable signal, is added and incubated, allowing time sufficient for the formation of a ternary complex of antibody-antigen-labeled antibody. Any unreacted material is then washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the CK1 polypeptide or related regulatory protein, substrate or fragments thereof.

The most commonly used reporter molecules are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of polypeptide or polypeptide fragment of interest which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

The pharmaceutical compositions of the present invention may also comprise substances that inhibit the expression of CK1 at the nucleic acid level. Such molecules include ribozymes, antisense oligonucleotides, triple helix DNA, RNA aptamers and/or double stranded RNA directed to an appropriate nucleotide sequence of CK1 nucleic acid. These inhibitory molecules may be created using conventional techniques by one of skill in the art without undue burden or experimentation. For example, modification (e.g. inhibition) of gene expression can be obtained by designing antisense molecules, DNA or RNA, to the control regions of the genes encoding the polypeptides discussed herein, i.e. to promoters, enhancers, and introns. For example, oligonucleotides derived from the transcription initiation site, e.g., between positions −10 and +10 from the start site may be used. Notwithstanding, all regions of the gene may be used to design an antisense molecule in order to create those which gives strongest hybridization to the mRNA and such suitable antisense oligonucleotides may be produced and identified by standard assay procedures familiar to one of skill in the art.

Similarly, inhibition of the expression of gene expression may be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). These molecules may also be designed to block translation of mRNA by preventing the transcript from binding to ribosomes.

Ribozymes, enzymatic RNA molecules, may also be used to inhibit gene expression by catalyzing the specific cleavage of RNA. The mechanism of ribozyme action involves sequence-specific hybridization of the ribozyme molecule to complementary target RNA, followed by endonucleolytic cleavage. Examples which may be used include engineered "hammerhead" or "hairpin" motif ribozyme molecules that can be designed to specifically and efficiently catalyze endonucleolytic cleavage of gene sequences, for example, the gene for CK1.

Specific ribozyme cleavage sites within any potential RNA target are initially identified by scanning the target molecule for ribozyme cleavage sites which include the following sequences: GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Ribozyme methods include exposing a cell to ribozymes or inducing expression in a cell of such small RNA ribozyme molecules (Grassi and Marini, 1996, Annals of Medicine 28: 499-510; Gibson, 1996, Cancer and Metastasis Reviews 15: 287-299). Intracellular expression of hammerhead and hairpin ribozymes targeted to mRNA corresponding to at least one of the genes discussed herein can be utilized to inhibit protein encoded by the gene.

Ribozymes can either be delivered directly to cells, in the form of RNA oligonucleotides incorporating ribozyme sequences, or introduced into the cell as an expression vector encoding the desired ribozymal RNA. Ribozymes can be routinely expressed in vivo in sufficient number to be catalytically effective in cleaving mRNA, and thereby modifying mRNA abundance in a cell (Cotten et al., 1989 EMBO J. 8:3861-3866). In particular, a ribozyme coding DNA sequence, designed according to conventional, well known rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. For saturating use, a highly and constitutively active promoter can be used. tDNA genes (i.e., genes encoding tRNAs) are useful in this application because of their small size, high rate of transcription, and ubiquitous expression in different kinds of tissues.

Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be modified or perturbed.

Ribozyme sequences can be modified in essentially the same manner as described for antisense nucleotides, e.g., the ribozyme sequence can comprise a modified base moiety.

RNA aptamers can also be introduced into or expressed in a cell to modify RNA abundance or activity. RNA aptamers are specific RNA ligands for proteins, such as for Tat and Rev RNA (Good et al., 1997, Gene Therapy 4: 45-54) that can specifically inhibit their translation.

Gene specific inhibition of gene expression may also be achieved using conventional RNAi technologies. Numerous references describing such technologies exist and include, for example, WO 99/32619; Miller et al. Cell Mol Neurobiol 25:1195-207 (2005); Lu et al. Adv Genet 54:117-42 (2005).

Antisense molecules, triple helix DNA, RNA aptamers and ribozymes of the present invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding the genes of the polypeptides discussed herein. Such DNA sequences may be incorporated into a wide variety of vectors with suitable RNA polymerase promoters such as T7 or SP6. Alternatively, cDNA constructs that synthesize antisense RNA constitutively or inducibly can be introduced into cell lines, cells, or tissues.

Vectors may be introduced into cells or tissues by many available means, and may be used in vivo, in vitro or ex vivo. For ex vivo therapy, vectors may be introduced into stem cells taken from the patient and clonally propagated for autologous transplant back into that same patient. Delivery by transfection and by liposome injections may be achieved using methods that are well known in the art.

In addition to the above described methods for inhibiting the gene expression of CK1, it is contemplated herein that one could identify and employ small molecules or other natural products to inhibit the transcription in vivo of the polypeptides discussed herein including, but not limited to, CK1. For example, one of skill in the art could establish an assay for CK1 that may be easily applied to samples from the culture media of a cell line using conventional methods. Using this assay, cell lines would be screened to find ones that express CK1 and would be cultured in, for example, 96 well plates. The closer the regulation of CK1 in the cell line to the expression in tissue in vivo, the more likely it will be that small molecule modifiers of CK1 expression in the cell lines will also modify CK1 in vivo. A comparison of the effects of some known modifiers of gene expression e.g. dexamethasone, phorbol ester, on the cell lines will allow the selection of the most appropriate cell line to use. The screen would then merely consist of culturing the cells for a set length of time with a different compound added to each well and then assaying for CK1 activity/mRNA level.

In order to faciliate the detection of CK1 in the assay described above, luciferase or other commercially available fluorescent protein could be genetically fused as an appropriate marker protein to the promoter of CK1. Sequences upstream of the ATG of CK1, i.e. the promoter of CK1, can be identified from genomic sequence data by using the sequence from GenBank human CK1 sequence GI:33873527 (e.g. as of Sep. 8, 2006) to BLAST against the NCBI genomic sequence. Two pairs of nested PCR primers to amplify a fragment of 2 kb or longer from human genomic DNA can be readily designed and tested. The promoter fragment can be readily inserted into any promoter-less reporter gene vector designed for expression in human cells (e.g. Clontech promoter-less enhanced fluorescent protein vector pECFP-1, pEGFP-1, or pEYFP). The screen could then consist of culturing the cells for an appropriate length of time with a different compound added to each well and then assaying for reporter gene activity. Promising compounds would then be assayed for effects on CK1 activity and/or mRNA level in vivo using, e.g., an in vivo model of Alzheimer's disease. Additional method details such as appropriate culturing time, culture conditions, reporter assays and other methodologies that may be used to identify small molecules or other natural products useful to inhibit the transcription of CK1 in vivo would be familiar to one of skill in the art.

In addition, the cDNA and/or protein of CK1 may be used to identify other proteins that may be modified by CK1 in vivo, e.g., in tissues in the nervous system. Proteins thus identified may be used for drug screening, e.g., to treat Alzheimer's disease. To identify genes that are downstream or upstream (especially relevant in case of post-translational modification) of CK1, it is contemplated, for example, that one could use conventional methods to treat animals in Alzheimer's disease models with a specific CK1 inhibitor, sacrifice the animals, remove appropriate tissue and isolate total RNA from these cells and employ standard microarray assay technologies to identify message levels that are altered relative to a control animal (animal to whom no drug has been administered).

Based on the knowledge that CK1 over expression induces an increase in Aβ peptide production, conventional in vitro or in vivo assays may be used to identify possible genes that, e.g., lead to over expression of CK1 or increased stability of CK1. These related regulatory proteins encoded by genes thus identified can be used to screen drugs that might be potent therapeutics for the treatment of Alzheimer's disease. For example, a conventional reporter gene assay could be used in which the promoter region of CK1 is placed upstream of a reporter gene (e.g. Luciferase, LacZ), the construct transfected into a suitable cell (for example, a HEK293, a CHO or a Hela cell line) and using conventional techniques, the cells may then be assayed for an upstream gene that causes activation of the CK1 promoter by detection of the expression of the reporter gene.

It is contemplated herein that one can inhibit the function and/or expression of a gene for a related regulatory protein or protein modified by CK1 or CK1 substrate as a way to treat an Aβ related disorder, e.g., Alzheimer's disease, by designing, for example, antibodies to these proteins and/or designing inhibitory antisense oligonucleotides, triple helix DNA, ribozymes and RNA aptamers targeted to the genes for such proteins according to conventional methods. Pharmaceutical compositions comprising such inhibitory substances for the treatment of said disorders are also contemplated.

The pharmaceutical compositions disclosed herein useful for treating Aβ related disorders, including Alzheimer's disease, are to be administered to a patient at therapeutically effective doses to treat symptoms of such disorders. A "therapeutically effective amount" is the amount of drug (e.g., CK1 modulator) sufficient to treat an Aβ related disorder. For example, a therapeutically effective amount of a CK1 modulator may be an amount shown to lessen or prevent the pathological accumulation of Aβ peptide that is seen in Alzheimer's disease and/or that can lessen or prevent the pathological effects of such accumulation. Improvements in the physical and/or mental state of an individual suffering from Alzheimer's disease may be measured by techniques and combinations of techniques familiar to one of skill in the art, including but not limited to, Clinical Dementia Rating (CDR) assessment, the mini-mental state exam (MMSE), the mini-cog exam, as well as positron emission tomography (PET), magnetic resonance imaging (MRI) and computed tomography (CT). Further diagnostic tests may include tests of biological fluids and tissues for various biochemical markers and activities.

Preferably, the compounds of the invention for use in the methods of treatment described herein are inhibitors of CK1. It is contemplated herein that this class of compounds may encompass structurally dissimilar compounds and includes, but is not limited to, CK1 inhibitors (a)-(i) discussed above. Other suitable CK1 inhibitors would be apparent to one of skill in the art. It is also contemplated that the CK1 inhibitors may act on any or all of CK1 isoforms, e.g., CK monomeric enzymes α, γ1, γ2, γ3, δ, ε1, ε2 and ε3.

CK1 modulators may be used in the methods disclosed herein as a sole therapeutic agent, but it is contemplated herein that they may also be used in combination with or for co-administration with other active agents. For example, any one or more CK1 modulators may be simultaneously, sequentially, or contemporaneously administered with conventional medications proven useful for the treatment of Alzheimer's disease. These medications include cholinesterase inhibitors such as Razadyne® (formerly known as Reminyl®) (galantamine), Exelon® (rivastigmine), Aricept® (donepezil), and Cognex® (tacrine) as well as Namenda® (memantine), an N-methyl D-aspartate (NMDA) antagonist. Additionally, drugs that have not yet been approved by the FDA for the treatment of Alzheimer's disease but which have recently been show to affect Aβ levels, may be used in combination in combination with or for co-administration with CK1 modulators discussed and contemplated herein. These drugs include such drugs as Gleevec (unidentified target(s)), GSK3β modulators/inhibitors (e.g. LiCl, Kenpaullone), and CDK5 modulators/inhibitors (e.g. roscovitine).

The present invention also provides (i) a CK1 modulator for use in the treatment of any disease or condition as hereinbefore set forth, or in a method of treatment as hereinbefore set forth;

(ii) the use of a CK1 modulator in the manufacture of a medicament for treating a disease or condition as hereinbefore set forth, or manufacture of a medicament for use in a method of treatment as hereinbefore set forth; and (iii) a pharmaceutical composition comprising a CK1 modulator in combination or association with a pharmaceutically acceptable diluent or carrier for use in the treatment of a disease or condition as hereinbefore set forth, or for use in a method of treatment as hereinbefore set forth.

The modulatory substances of the present invention can be administered as pharmaceutical compositions. Such pharmaceutical compositions for use in accordance with the present invention may be formulated in a conventional manner using one or more physiologically acceptable carriers or excipients.

Thus, the compounds and their physiologically acceptable salts and solvates may be formulated for administration by inhalation or insufflation (either through the mouth or the nose) or topical, oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of suitable cells, or in animal models. The animal model may also be used to determine the appropriate concentration range and route of administration. A dose may be formulated in animal models to achieve a circulating plasma concentration range that includes the $IC_{50}$ (i.e., the concentration of the test compound that achieves a half-maximal inhibition of symptoms). Such information can then be used to determine useful doses and routes for administration in humans.

With regard to a therapeutically effective dose of a CK1 modulator, therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Dosages employed in practicing the present invention will of course vary depending, e.g. on the particular disease or condition to be treated, the particular CK1 modulator used, the mode of administration, and the therapy desired. CK1 modulators for use in the instant invention may be administered by any suitable route, including orally, parenterally, transdermally, or by inhalation, but are preferably administered orally. In general, satisfactory results, e.g. for the treatment of diseases as hereinbefore set forth, are indicated to be obtained on oral administration at dosages of the order from about 0.01 to 10.0 mg/kg (all weights are given as the equivalent of CK1 modulator in free form, although the modulator may be provided in free or pharmaceutically acceptable salt form). In larger mammals, for example humans, an indicated daily dosage for oral administration will accordingly be in the range of from about 0.75 to 750 mg, e.g., 50-500 mg, conveniently administered once, or in divided doses 2 to 4 times daily, or in sustained release form. Unit dosage forms for oral administration thus for example may comprise from about 0.2 to 250 mg, e.g. from about 0.2 or 2.0 to 50, 75, 100 or 200 mg of CK1 modulator, together with a pharmaceutically acceptable diluent or carrier therefor.

The following examples further illustrate the present invention and are not intended to limit the invention.

EXAMPLES

Materials and methods relevant to the examples described herein are provided below:

Methods

Plasmids: Full length cDNAs corresponding to the four CK1 isoforms are subcloned from a rat oligonucleotide-dT cDNA library using standard PCR and molecular techniques into the pCDNA 3.1/Myc-6His A+ plasmid (Invitrogen). CK1 constitutively active constructs are derived from full length cDNAs by PCR and cloned into the pCDNA 3.1/Myc-6His A+ plasmid (Invitrogen). Subcloned DNA fragments are systematically checked by sequencing according to conventional methods. CK1α is truncated at amino acid 279; CK1 δis truncated at amino acid 271; CK1 εis truncated at amino acid 271; CK1γ is truncated at amino acid 307. C99 over-expressing plasmid is constructed by sub-cloning into the pCDN4 plasmid an APP DNA fragment coding for the membrane-bound C-terminal stub of APP produced after β-secretase cleavage.

Antibodies: Myc 9E10 (Covance), Cleaved Notch 1 (Val1744) (Cell Signaling Technology),Beta CTF and APP (polyclonal CT695) (Zymed), Beta-Actin (Cell Signaling Technology).

Kinase Inhibitors: CKI-7 (Japan), IC-261 (Calbiochem), D4476 (Calbiochem),DAPT (Calbiochem),Gleevec (Sequoia sciences, UK), L-685,458 (commercially available at EMD Biosciences). Stocks are prepared in dimethylsulphoxide (Sigma Aldrich) according to conventional methods.

Cell culture: Transfected N2A-APP$_{695}$ cells are grown as reported (Xu, H., et al., (1998) Nat Med 4, 447-51). N2A-APP$_{695}$ cells are plated in 12-well dishes at a density of 3×10$^5$ cells per well in DMEM/Opti-MEM medium containing 5% Fetal Bovine Serum (FBS) following manufacturer's instructions (American Type Culture Collection).= For the time-course experiments, cells are exposed to drugs for 1-24 h.

Transfection: Transfection of N2A-APP$_{695}$ cells is performed by standard methods. Cells are grown to 60% confluence and then transfected with relevant constructs with FUGENE6 according to the manufacturer's protocol (Roche Applied Bioscience). After transfection, cells are recovered with 100 µl of RIPA buffer, incubated for 30 min on ice, and centrifuged at 13,000 rpm 20 min at 4° C. The supernatants are collected and submitted to BCA (Pierce) quantification accordingly to manufacturer's instructions. Equal amounts of cell extracts are loaded onto 4-12% Bis-Tris acrylamide gels (Invitrogen) with MES buffer and subjected to western blot analysis using appropriate antibodies. For immunoprecipitation assays, media are incubated with antibody 4G8 (Signet) to detect Aβ and full length βAPP. Drugs are added to cell cultures in fresh medium (0.5% fetal bovine serum); media and cells are collected at the relevant time.

Aβ quantification: After immobilization of total Aβ (coated monoclonal antibody specific for the N-terminus of Aβ from media, Aβ40/42 peptide determinations are made by sandwich ELISA (BioSource International) using rabbit polyclonal antibodies specific for the C-terminus of Aβ40 or Aβ42. In all cases, Aβ levels are normalized to total protein levels.

Immunoprecipitation/Western Analysis: Immunodetection is carried out as previously reported in Xu, H., et al., (1998) Nat Med 4, 447-51 and using standard methods with the exception that Western blot analysis uses poly-vinylidene difluoride (PVDF) membranes (Invitrogen, Life Technologies) in PBS containing 0.2% glutaraldehyde (Sigma) for 45 min, after electrotransfer as described in Netzer, W J et al. Proc Natl Acad Sci USA. 2003 Oct. 14; 100(21):12444-9.

mNotchΔE Transfection and Notch-1 Cleavage Assays in N2A-APP$_{695}$ Cells: N2A cells stably overexpressing APP Swedish mutant are transiently transfected to overexpress mNotchE (truncated Notch-1, lacking most of the Notch extracellular domain (Kopan, R., et al. (1996) Proc Natl Acad Sci USA 93, 1683-8). Cultures are preincubated with the different inhibitors for 3 hours. mNotchΔE is detected in cell lysates by western blot analysis using the Cleaved Notch 1 antibody (NICD) available from Cell Signaling.

Example 1

In-Silico Analysis Reveals Conserved CK1 Consensus Phosphorylation Sites in APP, BACE and γ-Secretase The human, rat and mouse amino acid sequences corresponding to AD-related proteins (APP, BACE, PS1, PS2, Aph-1, PEN2 and Nicastrin) are screened for the presence of putative CK1 phosphorylation sites using different computational tools familiar to one of skill in the art (e.g. ELM-motifs, NetPhos 2.0). This in-silico analysis of intracellular domains in APP, BACE, PS1, PS2, Aph-1, PEN2 and Nicastrin reveal the presence of numerous conserved putative phosphorylation sites, particularly in PS1 and PS2 (data not shown).

Interestingly, the same in-silico analysis of the two kinases which have been implicated in AD (Cdk5/p35, and GSK3-β reveals the presence of numerous putative phosphorylation sites conserved in human, rat and mouse sequences. Indeed, we have found 7 putative sites in Cdk5, 15 in p35, and 24 in GSK3-β (data not shown).

Example 2

Over-Expression of Constitutively Active CK1ε leads to an Increase in Aβ Peptide Production We tested the capacity of four isoforms of CK1, namely CK1α, CK1β, CK1δ and CK1ε, to regulate APP processing by over-expressing each of the constitutively active isoforms. Constitutively active mutants are generated by truncating the C-terminal auto-inhibitory region of each isoform and expression levels are checked after transient transfection in N2A cells stably expressing APP (N2A-APP$_{695}$ cells) and data is normalized based on these levels. Data indicate that only CK1ε-271 is able to induce a substantial increase in Aβ peptide production. A slight effect is also observed for CK1δ-271 (data not shown).

We next compared the effect of over-expressing constitutively active CK1ε (CK1-271) versus full-length CK1ε (CK1ε-FL) in N2A cells stably expressing APP (N2A-APP$_{695}$ cells). Data indicate that CK1ε-271 induce an increase of Aβ-40 and Aβ-42 levels of 105% and 109% respectively (data not shown). In contrast, CK1ε full length is weakly active, producing an increase of Aβ40 and Aβ42 peptide levels of 42% and 31%, respectively (data not shown). These results, confirmed by Aβ peptide immunoprecipitation and western blotting analysis (data not shown), indicate that CK1 activity, is required for Aβ peptide regulation.

Example 3

Effect of CK1 inhibitors on Aβ peptide production following over-expression of constitutively active CK1ε in N2A-APP$_{695}$ cells We examined the effect of the selective CK1 inhibitor IC261 on Aβ40 and Aβ42 peptide production in N2A-

APP$_{695}$ cells transiently expressing CK1ε-271. N2A cells stably expressing APP-695 are transiently transfected with CK1ε-271. 48 hours post-transfection, cells are incubated in the absence or presence of increasing concentrations of CK1 inhibitor IC261. Cell supernatants are collected after 3 hours of incubation and subjected to Aβ40/Aβ42 ELISA assays. Results indicate that incubation with IC261 for three hours causes a dramatic reduction in Aβ40 and Aβ42 peptide concentration. The effect of IC261 is near maximum at 5 µM. IC261 had a time-dependent effect, with longer periods of exposure to IC261 resulting in greater reduction of Aβ40 and Aβ42 peptide concentration. In order to exclude non-specific effects of IC261, two other CK1 inhibitors, CKI-7 and D4476 are tested. Both inhibitors cause a significant and dose-dependent reduction of Aβ40 and Aβ42 production in CK1ε-271 over-expressing cells (data not shown).

Example 4

Regulation by CK1 Inhibitors of Endogenous Aβ Peptide Production

We next investigated the effect of the three different classes of CK1 inhibitors CKI-7, IC-261, and D4476 (Chijiwa, T., et al. (1989) *J Biol Chem* 264, 4924-7; Mashhoon, N., et al. (2000) *J Biol Chem* 275, 20052-60; Rena, G., et al. (2004) EMBO Rep 5, 60-5) on Aβ peptide production in N2A cells expressing APP-695. Data indicate that Aβ40 and Aβ42 peptide production is reduced after 3 hours of incubation with each of the three inhibitors (data not shown). The reduction is measured using two different methods: sandwich ELISA and western blotting analysis after immunoprecipitation (data not shown). We observed the following decreases upon incubation with 50 µM for three hours: IC261, 48% and 52.4% decrease for Aβ40 and Aβ42 peptides respectively, D4476, 42% and 54.1% decrease for Aβ40 and Aβ42 peptides respectively, and CKI-7, 14.8% and 24% decrease for Aβ40 and Aβ42 peptides respectively (data not shown). These results demonstrate that endogenous CK1, under basal conditions, participates in regulation of Aβ peptide production.

To exclude the possibility that the inhibitory effects on Aβ peptide production are due to cellular toxicity, we investigated the effects of the drugs on cell viability. Media are collected and tested for the level of lactate dehydrogenase, a stable cytosolic enzyme released upon cell lysis, using a non-radioactive CytoTox96 kit (Promega). Values obtained from drug treated cells are compared with values obtained with DMSO and non-treated cells. No toxicity is observed for CKI-7, even after 24 hours of incubation and for the highest concentration tested (50 µM). A slight toxicity (less than 1-fold) is observed for D4476, only for the higher dose tested (50 µM) and only after 24 hours of incubation. No effect on toxicity is observed with IC261 after 12 hours of incubation.

D4476 compound has been described recently as being a CK1 inhibitor and is described as being more potent and more selective in vitro than the two others (Rena, G., et al. (2004) EMBO Rep 5, 60-5.). However, a 50 µM concentration is required to observe an effect on CK1 activity in cell lines (Rena, G., et al. (2004) EMBO Rep 5, 60-5), suggesting that cellular permeability may be limiting. The 50 µM concentration used in those experiments is comparable with our results obtained using N2A-APP$_{695}$ cells.

Significantly, using the SMILE string notation for the D4476 compound, we have identified a compound very similar to D4476, namely SB-431542, which shows very comparable properties on Aβ peptide formation for both D4476 and SB-431542 (Sigma Aldrich) (data not shown).

Example 5

Effect of CK1 Inhibitor D4476 on APP, βCTF and Aβ levels

The effects of D4476 on APP, βCTF and Aβ40 peptide levels in N2A-APP$_{695}$ cells are compared. N2A cells are incubated for 3 hours with 0, 1, 5 or 50 µM concentrations of D4476. Cellular extracts are subjected to western blotting analysis using βCTF or APP antibodies, or to Aβ40 ELISA assays. N2A cells are transiently transfected with a APP-C99 containing plasmid. Twenty four hours post-transfection, cells are incubated with various concentrations of D4476 for 3 hours. Cell lysates are analyzed by SDS-PAGE and western blotting analysis or by Aβ40 ELISA assay. Data for at least three experiments (mean±S.E.M.) are compared (Prism) with the control conditions (no drug).

Results indicate that inhibition of CK1 with D4476 (50 µM) significantly increases βCTF levels and considerably reduces Aβ peptide production under conditions in which it had no effect on APP expression level. These results strongly suggest that CK1 activity regulates Aβ peptide formation at the level of γ-secretase cleavage site of APP and is necessary for Aβ peptide production. This conclusion is supported by experiments in which APP-C99 is expressed instead of the full length APP protein. D4476 inhibited the breakdown of C99 and consequently decreased Aβ peptide production in a dose dependent manner. These effects are apparent with as little as 5 µM of D4476 (data not shown).

Example 6

Notch Cleavage is not Affected by CK1 Inhibitors

Several protein kinases and protein phosphatases have been implicated in the progression of Alzheimer's disease and especially in the regulation of β-amyloid formation. These include the protein kinases PKA, PKC, GSK3-β and CDK5, and the protein phosphatases PP1/PP2A and PP2B. Early studies demonstrate that activation of PKA and PKC, or inhibition of PP1/PP2A and PP2B cause a dramatic reduction in the formation of β-amyloid and/or an increase in the amount of the α-secretase cleavage product sAPPα. Unfortunately, these effects are associated with increased carcinogenic risk. Indeed, a major side effect of γ-secretase inhibitors which have been developed for treatment of AD is inhibition of cleavage of Notch, a type I transmembrane protein which serves as a γ-secretase substrate; CDK5 inhibition (by Roscovitine) and GSK3 inhibition (by Kenpaullone) are at least partially associated with Notch cleavage inhibition. Thus, our data suggesting that CK1 inhibitors can reduce Aβ peptide reduction and can regulate Tau without affecting Notch cleavage, indicate that CK1 inhibitors are robust candidates for Alzheimer therapy. We therefore investigated the effect of CK1 inhibitors on Notch processing. Briefly, N2A cells transiently transfected with N-terminally truncated mNotchΔE-myc cDNA containing plasmid are incubated with 1, 10 µM concentrations of DAPT, 1,10 µM concentrations of L-685,458, 5, 50 µM concentrations of D4476 or 1, 10 µM concentrations of Gleevec for 3 hours. Cell lysates are analysed by conventional SDS-PAGE analysis and western blotting using anti-Notch (NICD cleavage product), anti-Aβ, anti-myc and anti-actin antibodies. Data for at least three experiments (mean±S.E.M.) are compared (Prism) with the control conditions (no drug). (**, P<0.01; one-tailed Student's t test, 95% significance level). Results indicate that in N2A cells over-expressing Notch, there is a total inhibition of Notch cleavage by DAPT. In contrast, Notch cleavage is not affected by D4476, IC261 or CKI-7 (data not shown), lending further interest to the possibility of developing CK1 and particularly CK1ε inhibitors for the treatment of AD.

Taken together, the data disclosed herein demonstrate that constitutively active CK1ε increases the formation of β-amyloid and distinct classes of CK1 inhibitors can reduce the formation of β-amyloid peptide produced both in N2A-$APP_{695}$ cells expressing endogenous levels of CK1 as well as over-expressing constitutively active CK1ε. Significantly, under conditions in which inhibition of CK1 activity reduces β-amyloid formation, no inhibition of Notch cleavage is observed. CK1 activity may possibly regulate Aβ peptide formation at the level of γ-secretase cleavage site of APP. The observations that structurally unrelated CK1 inhibitors can significantly decrease Aβ peptide production greatly reduces the possibility that these inhibitors act through a common target other than CK1. This conclusion is further supported by the fact that constitutively active CK1 leads to an increase in Aβ peptide formation and confirms the requirement of CK1 activity for the regulation of γ-secretase activity.

Example 7

Molecular Regulators of CK1 Activity as Novel Targets of Anti-AD Drugs

It is well established that phosphorylation of CK1ε in its carboxy-terminal region is associated with inhibition of CK1ε enzymatic activity. Conversely, dephosphorylation of CK1ε by calcineurin (or PP2B) leads to an activation of CK1 activity. The nature of the signal transduction pathway(s) responsible for the phosphorylation of CK1ε leading to a suppression of CK1 activity and for the activation of the PP2B/CK1 cascade remains to be characterized. One known mechanism for the activation of the PP2B/CK1 pathway involves a glutamate group I mGluR/Gq/PLC-IP3-$Ca^{2+}$ cascade. Once the mechanism by which CK1ε regulates Aβproduction is discovered, it will be of interest to further study the specific regulation of the three different CK1ε isoforms, namely CK1ε1, CK1ε2 and CK1ε3, each resulting from the expression of a distinct gene. The region used to test the impact of CK1ε constitutively active on Aβ peptide formation (N-terminal 271 amino acids) are 100% identical between the three isoforms; for this reason the present study only focuses on one of the three isoforms (CK1ε1). However, differences exist in their C-terminal regions and this could result in differences in term of kinase activity regulation based on fact that the C-terminal region is the regulatory region. Thus, the identification of such molecular regulators of CK1 activity may provide new targets for the development of anti-AD drugs. Several strategies may be employed to elucidate these regulatory molecules, such as phosphorylation studies, immunoprecipitation studies, and membrane fractionation studies to identify these CK1 regulators representing novel therapeutic targets. For example, one could conduct a kinase profiling type of experiment by testing a large panel of kinases for their ability to in-vitro phosphorylate CK1. The found kinases may be tested for their CK1 regulatory role by modulating their activity (or level of expression) in cell lines and by testing CK1 activity in-vitro after immunoprecipitation. Once confirmed, these kinases may be tested for their capacity to influence Aβ peptide production. The same type of experiment could be conducted to identify CK1 regulating phosphatases. Another possibility would be to look for CK1 binding proteins and test identified candidates for their ability to regulate CK1 activity in different systems such as in-vitro or in cell lines. CK1 binding proteins could be identified by mass spectrometry analysis after CK1 immunoprecipitation, SDS-PAGE and coomassie staining. Any other method that could help to identify protein-protein interaction such as yeast two-hybrid system, mammalian two-hybrid system, GST pull-down, could also be used to identify CK1 regulators.

Example 8

CK1 Subtrates as Novel Targets of Anti-AD Drugs

The identity of the substrate(s) by which CK1 regulates β-amyloid formation remains to be characterized. It is further contemplated herein that the identification of such substrate(s) may provide new targets for the development of anti-AD drugs. Several strategies may be employed such as phosphorylation studies, immunoprecipitation studies, and membrane fractionation studies to identify these novel targets. For example, phosphorylation studies may include 2D gel electrophoresis analysis. Briefly, membrane fractions containing APP are purified, radioactively labeled by conducting in-vitro CK1 phosphorylation and then analyzed by 2D gel electrophoresis. The profile obtained is compared with a profile realized in the same experimental conditions with the exception of the CK1 phosphorylation step. Differences in the profiles may reveal CK1 target proteins. These putative targets are identified by mass spectrometry analysis and their role in Aβ peptide generation tested by modulating their expression in a cellular system, for example, in N2A-$APP_{695}$ cells. Similar results may be obtained from APP co-immunoprecipitated proteins.

What is claimed is:
1. A method to identify a candidate modulator which reduces the accumulation of Aβ peptide levels in the brain, wherein the accumulation of Aβ peptide levels is reduced as compared to a control modulator, comprising assaying for the ability of a candidate modulator to inhibit Casein Kinase 1 ("CK1") activity by:
  a) providing a biological sample comprising or expressing a CK1 polypeptide;
  b) contacting said biological sample with a candidate modulator and measuring the phosphorylation activity and/or gene expression of CK1 in the biological sample after the sample has been contacted with the candidate modulator;
  c) contacting said biological sample with a control modulator wherein the control modulator is known to modulate the activity of CK1 and/or gene expression of CK1, and measuring the phosphorylation activity and/or gene expression of CK1 in the biological sample after the sample has been contacted with the control modulator;
  d) comparing CK1 phosphorylation activity and/or gene expression between the candidate and control modulators;
  e) selecting a candidate modulator for further testing based upon its ability to decrease the phosphorylation activity of CK1 and/or gene expression of CK1, and wherein the candidate modulator decreases the phosphorylation activity and/or gene expression of CK1 relative to the control modulator;

f) testing the candidate modulator in an animal model of an Aβ related disorder, wherein the candidate modulator is administered in said animal model and CK1phosphorylation activity and/or gene expression in the brain is measured after administration and compared to a control modulator in an animal model of an Aβ related disorder; and g) identifying a candidate modulator based upon its ability to decrease CK1phosphorylation activity and/or gene expression and reduce the accumulation of AB peptide in the brain of in the animal model.

2. The method according to claim 1 wherein said Aβ related disorder is Alzheimer's disease.

3. The method according to claim 1 wherein said method further comprises assaying for the ability of the candidate modulator to reduce the levels of Aβ peptide in brain tissue samples of animal models of an Aβ related disorder and/or in clinical studies with subjects with an Aβ related disorder comprising:

1) providing a biological sample comprising or expressing a Aβ peptide;
2) contacting said biological sample with the candidate modulator to be screened and measuring the levels of Aβ peptide in the biological sample after the sample has been contacted with the candidate modulator;
3) contacting said biological sample with a control modulator wherein the control modulator is known to reduce the levels of Aβ peptide and measuring the levels of Aβ peptide in the biological sample after the sample has been contacted with the control modulator;
4) comparing the levels of Aβ peptide between the candidate and control candidate modulators;
5) selecting a candidate modulator based upon its ability to decrease levels of Aβ peptide, and wherein a candidate modulator decreases the level of Aβ peptide relative to the control modulator;
6) testing a candidate modulator in an animal model and/or in a clinical study wherein the candidate modulator is administered in said animal model and levels of Aβ peptide are measured after administration and compared to a control; and
7) identifying a potential candidate modulator based upon its ability to decrease levels of Aβ peptide in the animal model and/or clinical study.

4. A method of claim 1, wherein the CK1 is Casein Kinase 1ε ("CK1ε").

* * * * *